United States Patent [19]

Ashida et al.

[11] Patent Number: 5,969,202

[45] Date of Patent: Oct. 19, 1999

[54] METHOD FOR PRODUCING CYCLOOLEFIN AND CYCLOALKANE UNDER CONTROLLED PRESSURE

[75] Inventors: Keita Ashida; Mineyuki Iwasaki, both of Kurashiki, Japan

[73] Assignee: Asahi Kasei Kogyo Kabushiki Kaisha, Osaka, Japan

[21] Appl. No.: 09/053,654

[22] Filed: Apr. 2, 1998

[30] Foreign Application Priority Data

Apr. 2, 1997 [JP] Japan .................................. 9-084187

[51] Int. Cl.$^6$ ................................. C07C 5/10; C07C 5/05
[52] U.S. Cl. ........................ 585/269; 585/266; 585/271; 585/273
[58] Field of Search ..................... 585/266, 269, 585/273, 271

[56] References Cited

U.S. PATENT DOCUMENTS

| 4,734,536 | 3/1988 | Nagahara et al. | 585/269 |
| 5,656,761 | 8/1997 | Nagahara et al. | 585/269 |

FOREIGN PATENT DOCUMENTS

| B2 5-12331 | 2/1993 | Japan . |
| B2 8-19012 | 2/1996 | Japan . |

OTHER PUBLICATIONS

C.U. Ingemar Odenbrand and Sten T. Lundin, "Hydrogenation of Benzene to Cyclohexene on a Ruthenium Catalyst: Influence of Some Reaction Parameters", J. Chem. Tech. Biotechnol.(1980) pp. 677–687.

J. Struijk, M. d'Angremond, W.J.M Lucas–de Regt and J.J.F. Scholten, "Partial liquid phase hydrogenation of benzene to cyclohexene over ruthenium catalysts in the presence of an aqueous salt solution", Applied Catalysis A: General, 83 (1992) pp. 263–295.

*Primary Examiner*—Walter D. Griffin
*Assistant Examiner*—In Suk Bullock
*Attorney, Agent, or Firm*—Birch, Stewart, Kolasch & Birch, LLP

[57] ABSTRACT

A method for producing a cycloolefin and a cycloalkane, which method comprises: a step of hydrogenating a monocyclic aromatic hydrocarbon under an acidic condition in the presence of a catalyst composition, (i) wherein said catalyst composition is a slurry which comprises a ruthenium catalyst, water and zinc sulfate, and which is preserved, prior to being used in said hydrogenation reaction, under a high temperature and high pressure hydrogen atmosphere of from 100 to 200° C. and from 1 to 100 atm for 1 hour or more, and (ii) wherein said hydrogenation reaction is conducted under a controlled pressure, while maintaining a phase separated state of: (a) an oil phase comprising, as main components, the starting materials and the products; and (b) a water phase comprising water as a main component, to thereby control a formation molar ratio of the cycloolefin and the cycloalkane to be formed.

11 Claims, No Drawings

METHOD FOR PRODUCING CYCLOOLEFIN AND CYCLOALKANE UNDER CONTROLLED PRESSURE

FIELD OF THE INVENTION

The present invention relates to a method for producing a cycloolefin and a cycloalkane concurrently by hydrogenating a monocyclic aromatic hydrocarbon in the presence of a ruthenium catalyst.

BACKGROUND OF THE INVENTION

Cycloolefins, in particular, cyclohexene compounds are valuable as intermediates of organic chemical industrial products, and are particularly useful as a starting material for polyamides and lysine.

On the other hand, cycloalkanes, in particular, cyclohexane compounds are industrially useful as an organic chemical product, particularly, as a starting material of caprolactam, adipic acid, etc. and as an organic solvent.

Various methods of producing cycloolefins are known. The most common method is a method of partially hydrogenating a monocyclic aromatic hydrocarbon using a ruthenium catalyst. In this method, an appreciable amount of cycloalkane, which is a completely hydrogenated product and a useful industrial starting material, is necessarily by-produced. Therefore, this method is substantially a method of producing a cycloolefin and a cycloalkane concurrently.

As a means for improving the selectivity and yield of cycloolefin, many results of examinations made for catalyst components, and kinds of carriers and metal salts as additives to reaction systems have been reported. Of these, as to the reaction system in which water and zinc coexist, which shows a relatively high molar ratio of cycloolefin formed, i.e., a relatively high selectivity of cycloolefin, the following methods are proposed for example.

(1) A method for partially reducing a monocyclic aromatic hydrocarbon with hydrogen in the presence of water and at least one kind of zinc compound under a neutral or acidic condition, using a particulate hydrogenating catalyst mainly comprising metallic ruthenium having an average crystallite size of 200 Å or less (JP-B-8-25919 (the term "JP-B" as used herein means an "examined Japanese patent publication") and U.S. Pat. No. 4,734,536).

(2) A method for producing a cycloolefin by partially hydrogenating a monocyclic aromatic hydrocarbon in the presence of a ruthenium catalyst, in which at least one of a zinc oxide and a zinc hydroxide at an amount of not more than saturation solubility is present in the reaction system in a completely dissolved state (JP-B-5-12331).

(3) A method for partially reducing a monocyclic aromatic hydrocarbon with hydrogen in the presence of water, in which a reaction is conducted using hydrogenated catalyst particles comprising metallic ruthenium having an average crystallite size of 200 Å or less as a main component in the presence of at least one kind of a solid basic zinc under a neutral or acidic condition (JP-B-8-19012).

Further, the influence of the reaction temperature and reaction pressure on the reaction result has been extensively studied. It is already well known that when the water phase in the reaction system shows an alkaline condition or when a ruthenium chloride is directly reduced in the reaction vessel and starting material is put in the reaction vessel to undergo reaction, an increase of the reaction temperature and reaction pressure results in the increase of the yield of cycloolefin produced (J. Chem. Tech. Biotechnol., 1980, 30, 677–687, etc.).

On the other hand, in the method of hydrogenating a monocyclic aromatic hydrocarbon using a ruthenium catalyst in the presence of water and zinc sulfate in an acidic condition with zinc sulfate being dissolved in water, the reaction pressure hardly has an influence on the initial formation ratio of the product, i.e., the product formation ratio at the starting material conversion ratio of around 0 mol % (Applied Catalysis A: General, 83 (1992) 263–295), which is knowledge generally accepted in the art and there have been no data contrary thereto. According to this thesis, the product formation ratio and the adsorbed amount of hydrogen onto the surface of the catalyst correlate to each other, and the product formation ratio does not change as long as the adsorbed amount of hydrogen does not change, even if the hydrogen pressure in the reaction vessel is changed. The thesis concludes that when the hydrogen pressure in the reaction vessel is increased, the consumption rate of the adsorbed hydrogen on the surface of the catalyst becomes fast because the conversion rate of the starting material becomes fast. As a result, the adsorbed amount of hydrogen on the surface of the catalyst hardly changes, therefore, the initial formation ratio of the product is hardly changed. As is easily presumed from the above knowledge, with a reaction system in which at least a ruthenium catalyst, zinc sulfate and water coexist, the product formation ratio cannot be controlled by changing gaseous phase hydrogen pressure in the reaction vessel, which is substantially the reaction pressure.

In the method of producing a cycloolefin by partially hydrogenating a monocyclic aromatic hydrocarbon using a ruthenium catalyst, cycloalkanes which are completely hydrogenated products are necessarily by-produced in addition to cycloolefins which are partially hydrogenated products, as described above. Cycloalkanes are useful industrial products which compare favorably with cycloolefins. Accordingly, upon performing this method industrially, the need to control or change the formation ratio of a cycloolefin and a cycloalkane arises in accordance with the fluctuation in demand of a cycloolefin and a cycloalkane. If the formation ratio cannot be controlled, disposition of the overproduced material or a big storage tank are required. Alternatively, production should be done with an adjusting of the scale to that of the smaller demanded material. This leads to a decrease in operation rate of the production facility.

That is, in the method of producing a cycloolefin by partially hydrogenating a monocyclic aromatic hydrocarbon using a ruthenium catalyst, if the formation ratio of a cycloolefin and a cycloalkane to be produced cannot be controlled, such a producing method is industrially extremely inefficient.

Furthermore, the stability of the catalyst and/or reaction system does not reach an industrially satisfactory level in conventional producing methods. Therefore, in the case where the production is continuously performed, the formation ratio of a cycloolefin and a cycloalkane can fluctuate even under almost identical reaction temperature and reaction pressure conditions, which cause a further need of adjustment.

Therefore, for industrially performing the production of a cycloolefin using ruthenium, controlling methods to adjust or change the formation ratio of the product are essential.

However, there have been the following four problems in conventional methods.

(1) Among the methods of producing a cycloolefin using a ruthenium catalyst, the proposed methods for performing the reaction under alkaline conditions provide a lower formation ratio of a cycloolefin product, as compared with the methods where the reaction is performed under acidic conditions in the presence of zinc sulfate and water. Accordingly, when the formation ratio of a cycloolefin is desired to be controlled within higher ranges, the controllable range is disadvantageously narrow even if the reaction temperature and reaction pressure are changed.

(2) On the other hand, with regard to the proposed methods of producing a cycloolefin under acidic conditions using zinc sulfate, water and a ruthenium catalyst, neither a specific controlling method of the formation ratio of the product nor a concept thereof has been suggested. Thus, for these methods, there has been no effective proposal for controlling the product formation ratio, which is required to be adjusted or changed in the case where the performance of the catalyst is changed or where some external disturbance happens and affects the reaction system, after starting the production.

(3) The product formation ratio can be controlled by the changing the reaction temperature. However, the change of the reaction temperature is accompanied by a large load fluctuation on the facilities to remove or recover the reaction heat. Therefore, control by only changing the reaction temperature is not a preferred controlling means.

(4) The product formation ratio can be controlled by varying the conversion rate of a starting material through characteristics of the reaction in the production method of a cycloolefin and a cycloalkane using a ruthenium catalyst, i.e., varying characteristics such that the higher the conversion rate of the starting material, the lower the formation ratio of cycloolefin formed, and the higher the formation ratio of cycloalkane instead. However, in this method, the concentration of the unreacted starting material contained in the product taken out from the reaction vessel fluctuates largely, and the load fluctuation in the step of separating the unreacted starting material is large. In particular, when a continuous reaction system of continuously feeding the starting material and continuously taking out the product is used, a large intermediate drum to absorb such fluctuation is required between the production facility and the subsequent separating and recovering step of the unreacted starting material, which is thus problematic and not preferred.

SUMMARY OF THE INVENTION

An object of the present invention is to provide an industrially practicable method for producing a cycloolefin and a cycloalkane, which overcomes the above-described problems at the same time, and with which the formation ratio of a cycloolefin and a cycloalkane can be easily adjusted.

Other objects and effects of the present invention will become apparent from the following description.

Upon producing a cycloolefin and a cycloalkane by hydrogenating a monocyclic aromatic hydrocarbon using a ruthenium catalyst, water and zinc sulfate in an acidic condition, the present inventors extensively studied to develop a method of controlling the formation ratio, i.e., the molar ratio of the formed cycloolefin and the formed cycloalkane. As a result, the present inventors have found that if a catalyst slurry which has been preserved under the specific high temperature high pressure hydrogen atmosphere for 1 hour or more is used, the formation ratio of the cycloolefin and the cycloalkane shows noticeable dependency on the reaction pressure. By utilizing this characteristic, control of the formation molar ratio of the formed cycloolefine and the formed cycloalkane has been achieved. The present invention is based on this finding.

That is, the objectives of the present invention have been achieved by the following constitutions.

(1) A method for producing a cycloolefin and a cycloalkane, which method comprises:
  a step of hydrogenating a monocyclic aromatic hydrocarbon under an acidic condition in the presence of a catalyst composition,
  (i) wherein said catalyst composition is a slurry which comprises a ruthenium catalyst, water and zinc sulfate, and which is preserved, prior to being used in said hydrogenation reaction, under a high temperature and high pressure hydrogen atmosphere of from 100 to 200° C. and from 1 to 100 atm for 1 hour or more, and
  (ii) wherein said hydrogenation reaction is conducted under a controlled pressure, while maintaining a phase separated state of:
    (a) an oil phase comprising, as main components, the starting materials and the products; and
    (b) a water phase comprising water as a main component, to thereby control a formation molar ratio of the cycloolefin and the cycloalkane to be formed.

(2) The method according to the above (1), wherein said hydrogenation reaction is conducted without changing a conversion rate of said monocyclic aromatic hydrocarbon.

(3) The method according to the above (1) or (2), wherein the reaction temperature of said hydrogenation reaction is from 100° C. to 200° C.

(4) The method according to the above (1), wherein said water phase has a zinc sulfate concentration of from 0.01 to 10 mol/liter.

(5) The method according to any one of the above (1) to (4), wherein the weight of said water phase is from 0.001 to 100 times the weight of said monocyclic aromatic hydrocarbon.

(6) The method according to any one of the above (1) to (5), wherein said ruthenium catalyst is a non-supported catalyst mainly comprising metallic ruthenium having an average crystallite size of 200 Å or less, said metallic ruthenium being obtained by reducing a ruthenium compound.

(7) The method according to the above (6), wherein said metallic ruthenium further contains a zinc compound, which is obtained by reducing a ruthenium compound containing a zinc compound, said metallic ruthenium having a zinc content of from 0.1 to 50% by weight based on the weight of ruthenium.

DETAILED DESCRIPTION OF THE INVENTION

The present invention is described in detail below.

Examples of the monocyclic aromatic hydrocarbon which can be used as a starting material in the present invention include benzene, toluene, xylene compounds and lower alkylbenzene compounds.

Catalysts containing metallic ruthenium obtained by reducing various ruthenium compounds are used as the ruthenium catalyst for use in the present invention. The ruthenium compounds are not particularly limited, and chlorides, bromides, iodides, nitrates, sulfates and hydroxides thereof and complexes containing various kinds of ruthenium may be used. As a reduction method, a contact reduction method using hydrogen or carbon monoxide, or a chemical reduction method using formaldehyde, sodium borohydride or hydrazine can be used. Further, a reduction treatment may be conducted in a gaseous phase or a liquid phase.

Further, as the ruthenium catalyst for use in the present invention, metallic ruthenium catalysts containing other metals may be used, which are obtained by adding other metals, e.g., zinc, chromium, molybdenum, tungsten, manganese, cobalt, nickel, iron, copper, gold, platinum, etc., before and/or after a reduction treatment stage of the ruthenium compounds. These metals may be added in the form of a salt such as chloride, nitrate or sulfate, a complex such as an ammine complex, or a metal compound such as a hydroxide or an oxide. When such a metal is used, the atomic ratio of other metals to the ruthenium atom is generally from 0.001 to 20. Zinc is particularly preferably used as such other metal. More particularly, zinc is preferably added before reduction treatment of the catalyst in the form of a salt such as chloride, nitrate or sulfate, the form of a complex such as an ammine complex, or the form of a zinc compound such as a hydroxide or an oxide in such an amount that provides metallic ruthenium containing zinc in an amount of from 0.1 to 50% by weight based on the weight of ruthenium after reduction treatment.

A ruthenium catalyst may be supported by a carrier for use. The carrier for use in the present invention is not particularly limited. Examples thereof include metals such as magnesium, aluminum, silicon, calcium, titanium, vanadium, chromium, manganese, cobalt, iron, nickel, copper, zinc, zirconium, hafnium and tungsten; oxides, composite oxides, hydroxides, sulfates and water-insoluble metal salts of these metals; and compounds and mixtures obtained by chemically or physically combining two or more of such substances that can be used as a carrier. Supporting methods of ruthenium include an adsorption method, an ion exchange method, an immersion method, a coprecipitation method and a dry fixing method. The supported amount of the ruthenium is not also limited, but generally from 0.001 to 20% by weight based on the weight of the carrier. However, the ruthenium for use in the present invention is preferably not supported by a carrier and used as it is.

When the ruthenium catalyst is not supported by a carrier and used as it is, the average crystallite size of the metallic ruthenium obtained by reduction is preferably 200 Å or less. If the average crystallite size of the metallic ruthenium is too large, the ruthenium surface area, on which the active point of the reaction is considered to be present, per unit weight of the ruthenium is reduced, to thereby disadvantageously reduce the catalytic activity. This may necessitate a large amount of a ruthenium catalyst in accordance with the method of the present invention, and thus is not preferred.

Water is present in the reaction system of the present invention and the amount thereof varies depending on the reaction system. However, the amount of water should be an amount such that an organic liquid phase comprising the starting material and the products as main components (i.e., oil phase) and a liquid phase comprising water as a main component (i.e., water phase) do not mingle with each other to form one phase. In other words, the amount of water for use in the present invention should be such an amount that provides a phase separation state of the oil phase and the water phase, i.e., a liquid two phase state of the oil phase and the water phase. Too large an amount of water is disadvantageous, because it necessitates a large reaction vessel. The weight amount of water is preferably from 0.001 to 100 times, more preferably from 0.5 to 20 times, the weight of the monocyclic aromatic hydrocarbon used as the starting material. The term "main component" as used herein means the component(s) which accounts for the maximum molar number among the components constituting the respective liquid phases.

Further, in the present invention, it is necessary that at least a part of the zinc sulfate that is present should be present in a state dissolved in the water phase, and the hydrogen ion concentration in the water phase which is coexistent with the reaction system, i.e., pH, should be less than 7 (i.e., acidic).

Zinc sulfate coexisting with the reaction system exists in a state where most parts thereof are dissolved in the water phase due to its property of having a large solubility in water. The concentration of zinc sulfate that is dissolved in the water phase is preferably from 0.01 to 10 mol/liter, more preferably from 0.05 to 5 mol/liter. A part of a zinc compound may be present as a solid without being dissolved, and the weight of the solid zinc compound in terms of zinc is preferably 100 times or less, more preferably 0.1 times or less, the weight of the ruthenium catalyst.

The reaction system in the present invention may contain metal salts similarly as in the conventionally known methods. Examples of the metal salt include: metals belonging to group I of the Periodic Table, e.g., lithium, sodium, potassium, etc.; metals belonging to group II, e.g., magnesium, calcium, etc. (Group number is according to IUPAC Inorganic Chemistry Nomenclature, revised edition (1989)); metal nitrates, chlorides, oxides, hydroxides, sulfates, acetates and phosphates of zinc, manganese, cobalt, copper, cadmium, lead, arsenic, iron, gallium, germanium, vanadium, chromium, silver, gold, platinum, nickel, palladium, barium, aluminum, etc.; and chemical and/or physical mixtures of two or more of these. Of these, the addition of a zinc salt, e.g., zinc hydroxide, zinc oxide, etc., is preferred. In particular, a double salt composed of zinc hydroxide and zinc sulfate is preferably used. The amount of the metal salt used is not particularly limited as long as the water phase can be maintained in an acidic state, but the weight of the metal salt used is generally from $1\times10^{-5}$ to $1\times10^5$ times the weight of ruthenium used. The metal salts may be present anywhere in the reaction system, and may be present in any form.

One or more organic substances having one or more hydroxyl groups may be present in the reaction system besides water. The amount thereof is not particularly limited. However, with regard to those which can dissolve therein water, a monocyclic aromatic hydrocarbon, and the products therefrom, i.e., cycloolefin and cycloalkane, under the reaction conditions, the amount should be within such a range that the water phase and the oil phase in the reaction system do not mingle with each other to one liquid phase. That is, the addition amount of the organic substances is limited to the range which can retain the reaction solution in a two phase state of the water phase and the oil phase.

In producing a cycloolefin and a cycloalkane by hydrogenating a monocyclic aromatic hydrocarbon using a ruthenium catalyst, water and zinc sulfate in an acidic condition, an important feature of the present invention resides in the use of the catalyst slurry preserved under a specific high temperature and high pressure hydrogen atmosphere for 1 hour or more, and controlling the hydrogenation reaction pressure while maintaining the oil phase comprising the starting material and the products as main components and the water phase comprising water as a main component in a separated state, to thereby control the formation molar ratio of the cycloolefin and the cycloalkane to be formed.

As is apparent from the suggestion in the above-described literature, Applied Catalysis A: General, 83 (1992) 263–295), it has been considered that it is difficult to control the formation ratio, i.e., the formation molar ratio, of the products obtained in the reaction which is conducted in the presence of a ruthenium catalyst and zinc sulfate under an acidic condition by changing the reaction pressure.

However, the present inventors found that in the case where a catalyst slurry comprising a ruthenium catalyst, water and zinc sulfate for use in the reaction is charged in a reaction vessel, and then the temperature is increased from normal temperature and the pressure is increased from normal pressure by the introduction of hydrogen, and after retaining this state for a while, the starting material of a monocyclic aromatic hydrocarbon is then put into the reaction vessel and subjected to reaction, the influence of the reaction pressure change on the formation ratio of the products surprisingly and markedly appears. Furthermore, when the dependency of the formation ratio of the products on the reaction pressure was examined with the catalyst slurry being retained under the reaction conditions for 1 hour or more while conducting hydrogenation of a monocyclic aromatic hydrocarbon, the influence of the reaction pressure change on the formation ratio of the products noticeably appeared similarly as in the above case where the hydrogenation reaction was conducted after the retention of the slurry under a high temperature high pressure hydrogen atmosphere without conducting hydrogenation of monocyclic aromatic hydrocarbon. That is, a phenomenon can be observed that the reaction pressure affects the formation ratio of the products, a cycloolefin and a cycloalkane, by using the catalyst slurry retained under a high temperature and high pressure hydrogen atmosphere for 1 hour or more, regardless of whether the monocyclic aromatic hydrocarbon starting material is present or absent during the retention. The reason why the description in the above-described literature and the results of the experiments made by the present inventors, that is, the formation ratio of the products has dependency on the reaction pressure, do not coincide with each other is presumably that the time spent exposing the catalyst slurry to a high temperature high pressure hydrogen atmosphere is different therebetween. It is presumed that the above phenomenon is due to the fact that some change occurs in the catalyst slurry by exposing the catalyst slurry to a high temperature and high pressure hydrogen atmosphere for a certain time or more, and the state of hydrogen to be adsorbed onto ruthenium in the presence of zinc sulfate under an acidic condition changes with the lapse of time. Because this phenomenon is considered to be peculiar to the system in which zinc sulfate is present under an acidic condition, it is also presumed that some change occurs in the action of zinc sulfate on ruthenium, particularly the action of suppressing the formation ratio of a cycloalkane, by the retention under a high temperature and high pressure hydrogen atmosphere.

The words "high temperature and high pressure hydrogen atmosphere" as used in the present invention mean a hydrogen atmosphere having a temperature of from 100 to 200° C. and a pressure of from 1 to 100 atm, preferably a hydrogen atmosphere having a temperature of from 110 to 160° C. and a pressure of from 20 to 90 atm.

When the temperature is lower than 100° C., it takes a long time for the effect of the retention under a high temperature and high pressure condition to appear, and therefore is industrially impracticable. On the other hand, when the temperature exceeds 200° C., the crystallite size of the ruthenium catalyst rapidly increases, to thereby largely reduce the activity of the catalyst, which is not preferred. Further, when the hydrogen pressure is less than 1 atm, the effect of the retention under a-high temperature and high pressure condition hardly appears, and while when it exceeds 100 atm, deterioration of the activity of the ruthenium catalyst is disadvantageously accelerated.

The retention time of the ruthenium catalyst under the high temperature and high pressure hydrogen atmosphere is 1 hour or more, preferably 22 hours or more.

The hydrogenation reaction pressure can be appropriately controlled, taking into account the intended formation ratio of a cycloolefin and a cycloalkane to be formed and the deterioration rate of the catalyst activity.

Furthermore, the formation ratio of the products can also be adjusted by changing the reaction temperature as well as changing the reaction pressure as described above. Therefore, by utilizing a change in the reaction temperature in combination with a change in the reaction pressure, the formation ratio of the products can be controlled over a wider range. The reaction temperature is preferably from 100 to 200° C.

The method of the present invention can be applied to both a batch type reaction system and a continuous type reaction system. In the batch type reaction system, the formation ratio of the products can be relatively easily changed by previously preparing ruthenium catalysts which give different formation ratios of the products and replacing the catalyst from one with another for every reaction. As compared thereto, the present invention is considerably effectively applied to the continuous type reaction system. This is because the continuous type reaction system has few opportunities for replacing catalysts in the nature thereof. Therefore, if the method of the present invention is used in the continuous type reaction system, the formation ratio of the products can be controlled depending on one's needs without suspending the producing facility.

By using the method of the present invention in a batch type reaction method or a continuous type reaction method, the formation ratio of a cycloolefin and a cycloalkane can be adjusted by changing the reaction pressure without positively changing the conversion rate of the starting material. Further, if the formation ratio of the products is deviated from the intended ratio because of the change of the catalyst performance or some other external disturbances, it is possible to keep the intended formation ratio by changing the reaction pressure. For example, in the reaction system in which the products having a cycloolefin selectivity of 60 mol % are obtained with the conversion rate of the starting material of 50 mol %, the selectivity of cycloolefin of more than 60 mol % can be obtained by merely increasing the reaction pressure without changing the conversion rate of the starting material. On the contrary, a cycloolefin selectivity of less than 60 mol % can be obtained by merely lowering the reaction pressure without changing the conversion rate of the starting material.

In the batch type reaction system, it is necessary to watch the transition of a conversion rate of the starting material for keeping the conversion rate at a constant value, by suitably taking out a part of the oil phase in the reaction vessel to conduct a composition analysis. However, even if such a watch is conducted, it is difficult to make the conversion rate of the starting material completely constant. Because of the above-described picking up for watching, the conversion rate of the starting material fluctuates from that estimated at the time of suspension of reaction by ±3 mol % as a control width. On the other hand, in the continuous type reaction system, the conversion rate of the starting material, ideally, does not change as long as the reaction conditions do not change. However, in an actual continuous reaction, the conversion rate of the starting material fluctuates by a little due to external disturbance or other reasons, even if one does not intend to change the reaction conditions. Therefore, the phrase "without changing the conversion rate of the starting material" as described above means that the conversion rate of the starting material is in the range of ±3 mol % of the estimated conversion rate at the time of suspension of the reaction. For example, supposing the estimated conversion rate of the starting material is 60%, the conversion rate of the starting material is regarded as constant as long as the conversion rate of the starting material is within the range of from 57 to 63 mol %.

The reaction with a constant conversion rate of the starting material can be achieved by appropriately adjusting the reaction temperature, oil phase/water phase ratio, the feeding amount of the starting material, the reaction time, etc.

In the method according to the present invention, there may be a case where the reaction rate of the monocyclic aromatic hydrocarbon starting material is changed by changing the reaction pressure or by changing the reaction pressure and the reaction temperature, even if other conditions are not changed. However, this can be easily adjusted by changing the catalyst activity by appropriate means, and therefore does not cause any problem.

The reaction pressure in the present invention is the pressure of the vapor phase at the uppermost part in the reaction vessel, which phase exists in contact with the liquid phases mainly comprising the catalyst slurry, the monocyclic aromatic hydrocarbon and the products, i.e., a cycloolefin and a cycloalkane. The reaction pressure is the sum of the saturated vapor pressure of the components in these liquid phases at the reaction temperature and the partial pressure of hydrogen introduced into the reaction vessel.

The average crystallite size of the ruthenium catalyst for use in the present-invention is the value calculated with Scherrer's equation using the expansion of the diffraction line width obtained by a common method, i.e., X-ray diffraction. Specifically, the value is calculated using the expansion of the diffraction angle (2θ) which has the maximum in the vicinity of 44° when a CuKα line is used as the X-ray source.

EXAMPLE

The present invention will be described in greater detail with reference to the following Examples and comparative Example, but the invention should not be construed as being limited thereto.

The formation ratio of cyclohexene and a cycloolefin shown in the Examples and comparative Example below represents the selectivities obtained from the following equations based on concentration analysis values in the experiment.

Selectivity of cyclohexene (%)=(mol number of cyclohexene formed by the reaction/P)×100

Selectivity of cyclohexane (%)=(mol number of cyclohexane formed by the reaction/P)×103

(mol number)=(mol number of cyclohexene formed by the reaction)+(mol number of cyclohexane formed by the reaction)

Further, the conversion rate of benzene which was used as a starting material represents the conversion rate obtained from the following equation based on the values of concentration analysis in the experiment.

Conversion rate of benzene (%)={(mol number of benzene consumed in the reaction)/(mol number of benzene supplied to the reaction vessel)}×100

Example 1

One-half (0.5) gram of ruthenium catalyst (average crystallite size: about 50 Å) containing 6 wt % of zinc, which was obtained by reducing ruthenium hydroxide, in which zinc hydroxide was previously contained, by a well-known method, 2.5 g of zirconia as a dispersant (average crystallite size: about 200 Å), 280 ml of water of normal temperature, and 49 g of $ZnSO_4 \cdot 7H_2O$ (extra fine grade, manufactured by Wako Pure Chemical Industries Ltd.) were charged in an autoclave having a content volume of 1 liter the inside of which had been coated with Teflon, the gas in the inside was sufficiently substituted with hydrogen, the reaction vessel was sealed, the temperature was increased to 150° C. while stirring at high speed by induction stirring, and then the pressure was increased to 30 atm by introducing high pressure hydrogen. The catalyst slurry was retained for 22 hours while maintaining this condition, i.e., at a pressure in the reaction vessel of 30 atm and at a temperature of 150° C. with stirring at high speed. Then, 80 ml of liquid benzene at 150° C. was fed by pressure in the autoclave at a time and subjected to reaction at a reaction pressure of 30 atm and at a temperature of 150° C. with stirring at high speed while feeding hydrogen by pressure. A part of the reaction solution was taken out over time during the reaction and the components in the oil were analyzed by gas chromatography. In this experiment, the reaction was performed under the condition in which at least the two phases, which are the oil phase and the water phase, were present. The conversion rate of benzene, the selectivities of cyclohexene and cyclohexane were determined based on the data of the concentration analysis of benzene, cyclohexene and cyclohexane obtained from the experiment. The relationship between the formation ratio of cyclohexene and cyclohexane at a benzene conversion rate of 40 mol % is shown below, which was obtained by interpolating the above determined selectivities. Further, the results obtained in an experiment conducted in the same manner as above, except for changing the retention pressure and the reaction pressure are also shown below.

| Retention pressure and reaction pressure (atm) | Selectivity of cyclohexene (%) | Selectivity of cyclohexane (%) |
| --- | --- | --- |
| 30 | 78 | 22 |
| 50 | 84 | 16 |
| 70 | 86 | 14 |

Example 2

Two-tenths (0.2) gram of ruthenium catalyst (average crystallite size: about 50 Å), which was obtained by reducing oxide by a well-known method, 1.0 g of zirconia as a dispersant (average crystallite size: about 200 Å), 320 ml of water of normal temperature, and 14 g of $ZnSO_4.7H_2O$ (extra fine grade, manufactured by Wako Pure Chemical Industrial Ltd.) were charged in an autoclave having a content volume of 1 liter the inside of which had been coated with Teflon, the gas in the inside was sufficiently substituted with hydrogen, the reaction vessel was sealed, the temperature was increased to 150° C. while stirring at high speed by induction stirring, then the pressure was increased to 30 atm by introducing high pressure hydrogen. The catalyst slurry was retained for 22 hours while maintaining this condition, i.e., at a pressure in the reaction vessel of 30 atm and at a temperature of 150° C. with stirring at high speed, then 80 ml of liquid benzene at 150° C. was fed by pressure in the autoclave at a time and subjected to reaction at a reaction pressure of 30 atm at 150° C. with stirring at high speed while feeding hydrogen by pressure. A part of the reaction solution was taken out over time during the reaction and the components in the oil were analyzed by gas chromotography. In this experiment, the reaction was performed under the condition in which at least the two phases of the oil phase and the water phase were present. The conversion rate of benzene, the selectivities of cyclohexene and cyclohexane were determined based on the data of concentration analysis of benzene, cyclohexene and cyclohexane obtained from the experiment. The relationship between the formation ratio of cyclohexene and cyclohexane at a benzene conversion rate of 40 mol % is shown below, which was obtained by interpolating the above selectivities. Further, the results obtained in the experiment conducted in the same manner as above, except for changing the retention pressure and the reaction pressure are also shown below.

| Retention pressure and reaction pressure (atm) | Selectivity of cyclohexene (%) | Selectivity of cyclohexane (%) |
| --- | --- | --- |
| 30 | 63 | 37 |
| 50 | 71 | 29 |
| 90 | 71 | 27 |

The above Examples 1 and 2, it can be seen that the formation ratio of the products is changed by changing pressure.

Example 3

A continuous reaction for 700 hours was conducted under the condition of 30 atm and 150° C. using a continuous reaction apparatus capable of: continuously supplying benzene and hydrogen to the reaction vessel; continuously taking out the catalyst slurry and the formed oil containing the unreacted benzene from the reaction vessel and separating the catalyst slurry and the unreacted benzene; and continuously returning the separated catalyst slurry to the reaction vessel. The catalyst slurry after this continuous reaction was recovered and the same amount of the catalyst slurry as the amount of the catalyst slurry charged in the autoclave in Example 1 was divided. Then, this divided portion of the catalyst slurry was charged in an autoclave having a content volume of 1 liter and the inside of which had been coated with Teflon, the gas in the inside was sufficiently substituted with hydrogen, the reaction vessel was sealed, the temperature was increased to 150° C. while stirring at high speed by induction stirring, then the pressure was increased to 30 atm by introducing high pressure hydrogen. Immediate after the termination of the pressure increase, 80 ml of liquid benzene of 150° C. was fed by pressure in the autoclave at a time and subjected to reaction at a reaction pressure of 30 atm and at 150° C. with stirring at a high speed while feeding hydrogen by pressure. A part of the reaction solution was taken out over time during the reaction and the components in the oil were analyzed by gas chromatography. In this experiment, the reaction was performed under the condition in which at least the two phases of the oil phase and the water phase were present.

The catalyst slurry used in the above continuous reaction of 700 hours was composed of 10 g of ruthenium catalyst (average crystallite size: about 50 Å) containing 6 wt % of zinc, which was obtained by reducing ruthenium hydroxide previously containing zinc hydroxide, 50 g of zirconia as a dispersant (average crystallite size: about 200 Å), 1,400 ml of water, and 245 g of $ZnSO_4$. $7H_2O$ (extra fine grade, manufactured by Wako Pure Chemical Industries Ltd.). The water contained in the formed oil which was separated during the continuous reaction was separated by cooling the oil and returned to the reaction vessel, to thereby prevent the water in the catalyst slurry from reducing. Further, the continuous reaction apparatus comprised an autoclave having a content volume of 3 liters and the inside of which had been coated with Teflon, the feeding rate of benzene during continuous reaction was 200 ml/hr, and the amount of the catalyst slurry and the formed oil containing the unreacted benzene taken out from the reaction vessel was 1000 ml/hr. The conversion rate of benzene, the selectivities of cyclohexene and cyclohexane were determined based on the data of concentration analysis for benzene, cyclohexene and cyclohexane obtained from the experiment. The relationship between the formation ratio of cyclohexene and cyclohexane at a benzene conversion rate of 40 mol % is shown below, which was obtained by interpolating the above selectivities. Further, the results obtained in an experiment conducted in the same manner as above, except for changing the retention pressure and the reaction pressure are also shown below.

| Retention pressure and reaction pressure (atm) | Selectivity of cyclohexene (%) | Selectivity of cyclohexane (%) |
| --- | --- | --- |
| 30 | 76 | 24 |
| 50 | 82 | 18 |
| 70 | 87 | 13 |

From the above Example 3, it can be seen that by retaining the catalyst slurry under a high temperature and high pressure hydrogen atmosphere while conducting the reaction, the formation ratio of the products also has dependency on the reaction pressure, that is, the formation ratio of the products is changed by changing the reaction pressure.

Example 4

A continuous reaction of 600 hours or more was conducted using the continuous reaction apparatus used in Example 3. The reaction conditions thereof were a reaction pressure of 50 atm and a reaction temperature of 150° C. with stirring. The catalyst slurry charged in the reaction vessel was composed of 2.5 g of ruthenium catalyst, 13 g of zirconia, 1,400 ml of water and 245 g of $ZnSO_4.7H_2O$. The ruthenium catalyst used had an average crystallite size of 50 Å and was prepared in the same manner as in Example 1, which was a ruthenium hydride catalyst containing 6 wt % of zinc. The catalyst slurry and the formed oil containing the unreacted benzene was continuously taken out from the reaction vessel and the catalyst slurry and the unreacted benzene were separated, and the separated catalyst slurry was continuously returned to the reaction vessel. The separated and cooled oil was continuously taken out to the outside of the reaction system, the components in the oil were analyzed by gas chromatography, and the conversion rate of benzene, and the selectivities of cyclohexene and cyclohexane were determined. The feed rate of benzene was appropriately adjusted during the experiment so as to reach the benzene conversion rate of 40±3 mol %. The required amount of hydrogen was continuously supplied. At the point when 600 hours had elapsed from the commencement of the reaction, the components in the oil were analyzed, then the reaction pressure was lowered to 30 atm and the components in the oil were analyzed again. Thereafter, the reaction pressure was increased to 70 atm and the components in the oil were analyzed again. The results obtained are shown below.

| Reaction pressure (atm) | Selectivity of cyclohexene (%) | Selectivity of cyclohexane (%) |
|---|---|---|
| 30 | 76 | 24 |
| 50 | 81 | 19 |
| 70 | 86 | 14 |

In the above continuous reaction, the reaction was performed under an acidic condition and under the condition in which at least the oil phase and the water phase were present.

In Example 4, the formation molar ratio of cyclohexene and cyclohexane, i.e., the selectivities, could be changed and controlled only by changing the reaction pressure, using the catalyst slurry retained under high temperature high pressure hydrogen for hours while conducting the reaction, while maintaining constant the conversion rate of the starting material and benzene. Further, the formation molar ratio could be controlled while continuously performing the reaction without suspending the reaction at all.

Comparative Example 1

A hydrogenation reaction of benzene was performed in the same manner as in Example 1, except that a previously prepared mixture composed of 0.5 g of the ruthenium catalyst prepared in the same manner as in Example 1, 0.2 g of $ZnSO_4.7H_2O$ (extra fine grade, manufactured by Wako Pure Chemical Industries Ltd.), 0.4 g of water and 4.0 g of zirconia (average crystallite size: about 200 Å), 5 ml of water, and 250 ml of 1-butanol were charged in an autoclave having a content volume of 1 liter, the inside of which had been coated with Teflon, and the amount of liquid benzene charged was changed to 100 ml. The conversion rate of benzene, the selectivities of cyclohexene and cyclohexane were determined based on the data of concentration analysis for benzene, cyclohexene and cyclohexane obtained from this reaction. The relationship between the formation ratio of cyclohexene and cyclohexane at a benzene conversion rate of 40 mol % is shown below, which was obtained by interpolating the above selectivities. Further, the results obtained in an experiment conducted in the same manner as above, except for changing the retention pressure and the reaction pressure are also shown below.

| Retention pressure and reaction pressure (atm) | Selectivity of cyclohexene (%) | Selectivity of cyclohexane (%) |
|---|---|---|
| 30 | 23 | 77 |
| 50 | 24 | 76 |
| 70 | 23 | 77 |

In this reaction system, the liquid phase did not have the two phases of a water phase and an oil phase. Instead, water, 1-butanol, the starting material and the reaction product formed a single liquid phase. Different from the results in Example 1, the formation ratio of cyclohexene and cyclohexane to be formed did not have dependency on the reaction pressure. Similar experiments were conducted using a primary alcohol having from 1 to 6 carbon atoms. The results obtained showed a similar tendency to the results of the experiment using 1-butanol, i.e., the formation molar ratio of cyclohexene and cyclohexane being formed did not have dependency on the reaction pressure. This means that the liquid phase in the reaction system should have the two phases of the water phase and the oil phase for the formation ratio of the products to have the dependency on the reaction pressure. The reason why the formation ratio of cyclohexene was lower than the case in which the reaction was conducted with the two phases of the water phase and the oil phase is presumably that this was largely the result of mass transfer due to the conventionally considered solubility difference of cyclohexene and cyclohexane inbetween the liquid phases. The fact that the liquid phase was composed of one phase and did not consist of the two phases of a water phase and an oil phase in these reaction systems, was confirmed visually in the following manner. The catalyst, other additives including alcohol, benzene, cyclohexene and cyclohexane used in comparative Example 1 were mixed in the same amounts as in comparative Example 1, respectively, which was charged in a glass autoclave, highly stirred under pressure with $N_2$ at 150° C., then allowed to stand, and the liquid phase was confirmed to be a single phase.

In contrast, with respect to the use of a liquid phase being composed of two phases, this is done by making the amount of alcohol to be added smaller than that in comparative Example 1. For example, in the case of using the same catalyst as in comparative Example 1, charging 245 ml of water, 10 ml of hexanol, and 100 ml of benzene in an autoclave having a content volume of 1 liter, the inside of which had been coated with Teflon, and conducting the same experiment as in Example 1, the formation ratio of the products showed a dependency on the reaction pressure.

In Examples 1 to 3 and comparative Example 1, hydrogen ion concentration of the catalyst slurry, i.e., pH, was acidic, being less than 7.

According to the method of the present invention, the formation ratio of a partially hydrogenated product of a monocyclic aromatic hydrocarbon, i.e., a cycloolefin, and a completely hydrogenated product of a monocyclic aromatic hydrocarbon, i.e., a cycloalkane, can be industrially easily controlled.

While the invention has been described in detail and with reference to specific examples thereof, it will be apparent to one skilled in the art that various changes and modifications can be made therein without departing from the spirit and scope thereof.

What is claimed is:

1. A method for producing a cycloolefin and a cycloalkane, which method comprises:

hydrogenating a monocyclic aromatic hydrocarbon under an acidic condition in the presence of a catalyst composition; and controlling the molar ratio of the cycloolefin and the cycloalkane produced thereby by controlling the pressure in the hydrogenation reaction system, (i) wherein said catalyst composition is a slurry which comprises a ruthenium catalyst, water and zinc sulfate, and which is preserved, prior to being used in said hydrogenation reaction, under a high temperature and high pressure hydrogen atmosphere of from 100 to 200° C. and from 1 to 100 atm for 1 hour or more, and (ii) wherein said hydrogenation reaction is conducted while maintaining a phase separated state of:

(a) an oil phase comprising, as main components, the starting materials and the products; and (b) a water phase comprising water as a main component.

2. The method according to claim 1, wherein said hydrogenation reaction is conducted without changing a conversion rate of said monocyclic aromatic hydrocarbon.

3. The method according to claim 1, wherein the reaction temperature of said hydrogenation reaction is from 100° C. to 200° C.

4. The method according to claim 1, wherein said water phase has a zinc sulfate concentration of from 0.01 to 10 mol/liter.

5. The method according to claim 1, wherein the weight of said water phase is from 0.001 to 100 times the weight of said monocyclic aromatic hydrocarbon.

6. The method according to claim 1, wherein said ruthenium catalyst is a non-supported catalyst mainly comprising metallic ruthenium having an average crystallite size of 200 Å or less, said metallic ruthenium being obtained by reducing a ruthenium compound.

7. The method according to claim 6, wherein said metallic ruthenium further contains a zinc compound, which is obtained by reducing a ruthenium compound containing a zinc compound, said metallic ruthenium having a zinc content of from 0.1 to 50% by weight based on the weight of ruthenium.

8. The method according to claim 1, wherein said monocyclic aromatic hydrocarbon is selected from the group consisting of benzene, toluene, xylene compounds, and lower alkylbenzene compounds.

9. The method according to claim 1, wherein said ruthenium catalyst is supported by a carrier.

10. A method for producing a cycloolefin and a cycloalkane, which method comprises:

hydrogenating a monocyclic aromatic hydrocarbon under an acidic condition in the presence of a catalyst composition; and controlling the molar ratio of the cycloolefin and the cycloalkane produced thereby by controlling the pressure in the hydrogenation reaction system, (i) wherein said catalyst composition is a slurry which comprises a ruthenium catalyst, water and zinc sulfate, and which is retained under a high temperature and high pressure hydrogen atmosphere of from 100 to 200° C. and from 1 to 100 atm for 1 hour or more, and (ii) wherein said hydrogenation reaction is conducted while maintaining a phase separated state of:

(a) an oil phase comprising, as main components, the starting materials and the products; and (b) a water phase comprising water as a main component.

11. The method according to claim 10, wherein said hydrogenation reaction is conducted without changing a conversion rate of said monocyclic aromatic hydrocarbon.

* * * * *